United States Patent [19]
Kunz et al.

[11] Patent Number: 6,106,579
[45] Date of Patent: Aug. 22, 2000

[54] COMPOSITIONS AND METHODS FOR DYEING AND SAFE DECOLORIZING OF FIBERS, ESPECIALLY HAIR, AND MULTI-PART KIT FOR REPEATEDLY CHANGING DYED FIBER COLOR

[75] Inventors: Manuela Kunz; Dominique Le Cruer, both of Marly; Christel Dousse, Treyvaux, all of Switzerland

[73] Assignee: Wella Aktiengesellschaft, Darmstadt, Germany

[21] Appl. No.: 09/210,022

[22] Filed: Dec. 11, 1998

[30] Foreign Application Priority Data

Mar. 12, 1998 [DE] Germany ............ 198 10 688

[51] Int. Cl.$^7$ ............ A61K 7/13; A61K 7/135; D06L 3/10

[52] U.S. Cl. ............ 8/432; 8/405; 8/406; 8/431; 8/102; 8/107; 8/110; 252/188.1; 252/188.2; 252/188.21; 252/188.25; 132/208; 424/62

[58] Field of Search ............ 8/405, 406, 431, 8/432, 127.6, 128.3, 102, 107, 110; 132/208; 252/188.1, 188.21, 188.25, 188.28, 188.2; 424/70.6, 62

[56] References Cited

U.S. PATENT DOCUMENTS

| | | | |
|---|---|---|---|
| 2,149,319 | 3/1939 | Soussa | 424/62 |
| 2,236,970 | 4/1941 | Goldfarb | 424/62 |
| 3,218,234 | 11/1965 | Wilsmann | 424/70.6 |
| 3,816,615 | 6/1974 | Zeffren et al. | 424/62 |
| 3,838,966 | 10/1974 | Barchas et al. | 8/405 |
| 3,892,845 | 7/1975 | Cunningham et al. | 424/62 |
| 4,129,415 | 12/1978 | Westman | 8/102 |
| 4,244,690 | 1/1981 | Sato et al. | 8/465 |
| 5,198,465 | 3/1993 | Dioguardi | 514/474 |
| 5,651,960 | 7/1997 | Chan et al. | 424/70.6 |
| 5,782,933 | 7/1998 | Wis-Surel et al. | 8/431 |

FOREIGN PATENT DOCUMENTS

| | | |
|---|---|---|
| 0 310 675 | 4/1989 | European Pat. Off. . |
| 19546032 | 6/1997 | Germany . |
| 98/22078 | 5/1998 | WIPO . |

OTHER PUBLICATIONS

K. Schrader: "Grundlagen Und Rezepturen Der Kosmetika", Huethig Buch Verlag, Heidelberg, 1989, pp. 64–65, 217–219 and 80. No month available.

Phompp Chemie Lexicon, 9th Edition, J. Falbe, M. Regits, Eds., Georg Thleme Press, Stuttgart, New York, pp. 265–266, 4380–4381, 4589–4590 (1989, 1991). No month available.

Stephan Jellinek: "Kosmetologie", 3–d Edition, Huethig Press, Heodelberg (1976), p. 676. No month available.

G. Wenske, Woerterbuch Chemie, VCH Verlaggesellschaft MBH (VCH Press), Weinheim, New York, Basel, Cambridge, Tokyo, 1994. (no month available).

English language translation of FR 2,657,781, L'Oreal, pp. 1–31, Aug. 1991.

*Primary Examiner*—Caroline D. Liott
*Attorney, Agent, or Firm*—Michael J. Striker

[57] ABSTRACT

The method for decolorizing fibers includes applying a decolorizing composition according to the invention to dyed fibers and allowing the composition to act on the fibers for a sufficient time to remove dyed color from the dyed fibers. The decolorizing composition for fibers dyed with an oxidation hair dye composition and/or direct-dyeing hair dye compounds contains a combination of one or more α-oxocarboxylic acids and/or physiologically compatible α-oxocarboxylic acid salts with at least one reductone, or with at least one reductone and at least one thiol compound, or with at least one reductone and at least one sulfite compound, or with at least one reductone and at least one thiol compound and at least one sulfite compound. A multipart kit for repeatedly dyeing and subsequently decolorizing fibers, especially human hair, contains both a dye composition for dyeing the fibers and the above-described composition for reductive decolorizing of the dyed fibers.

17 Claims, No Drawings

6,106,579

COMPOSITIONS AND METHODS FOR DYEING AND SAFE DECOLORIZING OF FIBERS, ESPECIALLY HAIR, AND MULTI-PART KIT FOR REPEATEDLY CHANGING DYED FIBER COLOR

BACKGROUND OF THE INVENTION

The subject matter of the present invention includes a composition for decolorizing fibers and a process for decolorizing fibers using that composition as well as a multi-part kit for dyeing and subsequently decolorizing of fibers, especially human hair, which contains both a composition for dyeing the fibers and also the composition according to the invention for decolorizing the fibers.

Oxidative dye compositions are outstandingly suited for covering a large portion of gray. The oxidative dye compositions used to dye hair which is up to about 50% gray are called tinting compositions, while the oxidative dye compositions usually used to dye hair that is up to 100% grey color or for brightly coloring hair are called oxidative hair dyes.

Direct-dyeing dye compounds, especially nitro dye compounds, are widely used in non-oxidative dye compositions. Because of their small size they are able to penetrate in the hair and to directly dye at least the outer portions of the hair. This sort of dyeing is very safe and usually stands up to several hair washings.

Direct-dyeing dye compounds, especially nitro dye compounds, are frequently used in oxidative dye compositions to produce certain nuances or for intensifying the dyeing. Generally colored polymers produced oxidatively in the hair have a high resistance to external influences, such as water, shampoo or light. According to the dyeing arts they are firmly anchored so that generally they remain in the hair until the next hair cut. If removal of the dyed color is desired, a comparatively reactive chemical, such as formaldehyde-sulfoxylate, hydrogen peroxide or hydrogen peroxide addition products may be used. An extensive decolorizing or bleaching is also possible, however this type of treatment can damage the hair or have a deleterious effect on the health of the individual treated.

A partial decolorizing of non-oxidatively tinted hair is usually possible by multiple hair washings, but a complete removal of the color of the dyed hair is not possible in this way.

If a special hair color is desired, but for only a short time, the hair must first be dyed and then bleached again in a comparatively short time. The removal of the hair color under mild and safe conditions with either oxidative or non-oxidative agents has not been possible up to now.

SUMMARY OF THE INVENTION

It is an object of the present invention to provide a method for temporarily dyeing fibers, especially human hair, and for subsequently removing the dye color from the fibers after a comparative short time interval, which does not have the above-described disadvantages.

It is also an object of the present invention to provide compositions for performing the aforesaid method according to the invention.

It is an additional object of the invention to provide a composition for removal of color from hair that has been dyed with a hair dye composition that is more mild and gentle than prior art decolorizing compositions.

According to the invention this object is attained, in part, by a method of decolorizing hair with a combination of a) at least one reductone, especially ascorbic acid, and/or a thiol and/or a sulfite, and b) at least one α-oxocarboxylic acid or its physiologically compatible salt.

The use of ascorbic acid in hair care or hair dye compositions is known. For example, the use of an aqueous solution of ascorbic acid for removal of residues of hydrogen peroxide, which remain on human hair after an oxidative treatment is disclosed in EP-PS 0 401 454. Bath tablets containing ascorbic acid, which dissolve immediately when added to water, are suitable for this purpose.

The use of ascorbic acid to stabilize or maintain an otherwise unstable liquid hair dyeing composition is described in DE-OS 1 444 216. Also an oxidation hair dye composition containing ascorbic acid as a stabilizer is disclosed also in DE-OS 3 642 097. Thus the fact that ascorbic acid can be advantageously used for reductive decolorizing of the dyed colors from fibers, especially human hair, is the more surprising.

The subject matter of the invention also includes a multi-part kit for dyeing and later decolorizing fibers, especially hair, which includes a first part (I) containing an oxidative or non-oxidative dye composition for fibers, especially for human hair, and another part (II) for reductive decolorizing of the hair color from the hair that contains a) at least one reductone and/or a thiol and/or a sulfite, and b) at least one α-oxocarboxylic acid or its physiologically compatible salt.

DE-OS 42 16 667 discloses the use of α-ketodicarboxylic acids (especially α-ketoglutaric acid) or their physiologically compatible salts for removal of hydrogen peroxide residues from hair. JP-OS 63 101 307 discloses a cell activator for hair growth requirements, for example α-ketoglutaric acid.

The multi-part kit according to the invention contains a means of producing an oxidative dyeing agent (Part (I)) which is usually a mixture of two components, namely a dye carrier, which contains the oxidative dye pre-cursor compounds designated as couplers and developers and optional direct dye compounds and an oxidizing agent that is added to the dye carrier immediately prior to use for forming the dyeing agent, or a means for producing a non-oxidative dyeing agent (Part (I)) which is usually a one-component preparation for non-oxidative dyeing.

The multi-part kit according to the invention for oxidative dyeing contains at least one dye precursor compound suitable for formation of an oxidative dyeing agent in the dye carrier as developer substance. The following compounds are particularly suitable for that purpose: 1,4-diaminobenzene (p-phenylenediamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylamino-aniline, 4-[di(2-hydroxy-ethyl)amino]-aniline, 4-[(2-methoxyethyl)amino]-aniline, 4-[(3-hydroxy-propyl)-amino]aniline, 1,4-diamino-2-(2-hydroxy-ethyl)benzene, 1,4-diamino-2-(1-methylethyl)benzene, 1,3-bis-[(4-aminophenyl)-(2-hydroxyethyl)amino]-2-propanol, 1,8-bis-(2,5-diaminophenoxy)-3,6-dioxaoctane, 4-aminophenol, 4-amino-3-methylphenol, 4-methylaminophenol, 4-amino-2-(aminomethyl)-phenol, 4-amino2-[(2-hydroxyethyl)amino]-methylphenol, 4-amino-2-(methoxymethyl)phenol, 4-amino-2-(2-hydroxy-ethyl)phenol, 5-aminosalicylic acid, 2,5-diamino-pyridine, 2,4,5,6-tetraaminopyrimidine, 2,5,6-triamino-4-1H-pyrimidone, 4,5-diamino1-(2-hydroxyethyl)-1H-pyrazole, 4,5-diamino-1-(1- methylethyl)-1H-pyrazole, 4,5-diamino-1-[(4-methylphenyl)methyl]-1H-pyrazole, 1-[(4-chlorophenyl)-methyl]-4,5-diamino-1H-pyrazole, 4,5-diamino-1-methyl-1H-pyrazole as well as 2-aminophenol, 2-amino-6-methylphenol, 2-amino-5-methylphenol and/or their salts.

The dye carrier for oxidative dyeing also contains at least one coupler compound suitable for forming an oxidative dyeing agent. Aromatic m-diamines, m-aminophenols, polyphenols or naphthols may be used as coupler compounds. The following coupler compounds are particularly suitable: N-(3-dimethylamino-phenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diamino-benzene, 2,4-diamino-1-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)-phenol, 3-[(2-hydroxyethyl)amino]aniline, 3-[(2-aminoethyl)amino]-aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methyl-phenol, 5-amino-4-methoxy-2-methyl-phenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methylphenol, 3-aminophenol, 2-[(3-hydroxyphenyl)amino]-acetamide, 5-[(2-hydroxyethyl)amino]2-methylphenol, 3-[(2-hydroxyethyl)amino]phenol, 3-[(2-methoxyethyl)amino]-phenol, 5-amino-2-ethyl-phenol, 2-(4-amino-2-hydroxyphenoxy)ethanol, 5[(3-hydroxypropyl)amino]-2-methyl-phenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylendioxyphenol, 3,4-methylenedioxyaniline, 5-[(2-hydroxyethyl)amino]-1,3-benzodioxole, 6-bromo-1-hydroxy3,4-methylendioxybenzene, 3,4-diaminobenzoic acid, 3,4-dihydro6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolinedione and/or their salts.

The developer substance or coupler substance is contained in the dye carrier in an amount of about 0.01 to 10 percent by weight, preferably from 0.1 to 5 percent by weight.

Furthermore the dye carrier containing the oxidative dyeing agent can also contain non-oxidative dye compounds (designated as "direct-dyeing dye compounds" in the following) as needed, for example 1,4-bis-[(2-hydroxyethyl)amino]-2-nitrobenzene, 1-(2-hydroxyethyl)amino-2-nitro-4[di(2-hydroxyethyl)amino]benzene (HC Blue No. 2), 1-amino-3-methyl4-[(2-hydroxyethyl)amino]-6-nitrobenzene (HC Violet No.1), 4-[ethyl-(2-hydroxyethyl)-amino]-1-(2-hydroxyethyl)amino]-2 nitrobenzene hydrochloride (HC Blue No. 12), 4-[di(2-hydroxyethyl) amino]-1-[(2-methoxy-ethyl)amino]-2-nitrobenzene (HC Blue No. 11), 1-[(2,3-dihydroxypropyl)amino]-4-[methyl(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxy-ethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethylamino-benzoic acid (HC Blue No. 13), 1-amino-4-[(2-hydroxyethyl)-amino]-2-nitrobenzene (HC Red No. 7), 2-amino-4,6-dinitro-phenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene(HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4'-amino-2'-nitrophenyl)amino]benzoic acid, 2-chloro-6-ethylamino-4-nitrophenol, 2-amino-6-chloro4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamin-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[(2,3-dihydroxypropyl)amino]-9,10-anthraquinone, 1-[(2-hydroxyethyl)amino]-4-methylamino-9,10-anthraquinone (CI 61505, Disperse Blue No. 3), 2-[(2-aminoethyl)amino]-9,10-anthraquinone (HC Orange No. 5),1-hydroxy- 4[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI 62015, Disperse Red No. 11, Solvent Violet No. 26), 1,4-dihydroxy-5,8-bis-[(2-hydroxyethyl)

amino]-9,10-anthraquinone (CI 62500, Disperse Blue No. 7, Solvent Blue No. 69), 9-(dimethylamino)benzo[a] phenoxazin-7-ium-chloride (CI 51175; Basic Blue No. 6), di[4-(diethylamino)phenyl][4-(ethylamino)naphthyl] carbenium chloride (CI 42595; Basic Blue No. 7), 3,7-di (dimethylamino)phenothiazin-5-ium chloride (CI 52015; Basic Blue No. 9), di[4-(dimethylamino)phenyl]-[4-(phenylamino)naphthyl]carbenium chloride (CI 44045; Basic Blue No. 26), 2-[(4-(ethyl-(2-hydroxyethyl)amino) phenyl)azo]-6-methoxy3-methylbenzothiazolium methyl sulfate (CI 11154; Basic Blue No. 41), 8-amino-2-bromo-5-hydroxy-4-imino-6-[(3-(trimethylammonio)phenyl) amino]-1(4H)-naphthalenone chloride (CI 56059; Basic Blue No. 99), bis-[4-(dimethylamino)phenyl]-[4-(methylamino)phenyl]carbenium chloride (CI 42535; Basic Violet No. 1), tris-[4-(dimethylamino)phenyl]carbenium chloride (CI 42555; Basic Violet No. 3), 2-[3,6-(diethylamino)dibenzopyranium-9-yl]-benzoic acid chloride (CI 45170; Basic Violet No. 10), di(4-aminophenyl)(4-amino-3-methylphenyl)carbenium chloride (CI 42510; Basic Violet No. 14), 1,3-bis[(2,4-diamino5-methylphenyl) azo]-3-methylbenzene (CI 21010; Basic Brown No. 4), 1-[(4-aminophenyl)azo]-7-(trimethylammonio)-2-naphthol chloride (CI 12250; Basic Brown No. 16), 1-[(4-amino-2-nitrophenyl)azo]-7-(trimethylammonio)-2-naphthol chloride (Basic Brown No. 17), 1-[(4-amino-3-nitrophenyl)-azo]-7-(trimethylammonio)-2-naphthol chloride (CI 12251; Basic Brown No. 17), 3,7-diamino-2,8-dimethyl-5-phenyl-phenazinium chloride (CI 50240; Basic Red No. 2), 1,4-dimethyl-5-[(4-(dimethylamino)phenyl)azo]-1,2,4-triazolium chloride (CI 11055; Basic Red No. 22), 2-hydroxy-1-[(2-methoxyphenyl)azo]-7-(trimethylammonio)naphthalene chloride (CI 12245; Basic Red No. 76), 2-[2-((2,4-dimethoxyphenyl)-amino)ethenyl]-1,3,3-trimethyl-3H-indol-1-ium chloride (CI 48055; Basic Yellow No. 11),3-methyl-1-phenyl-4-[(3-(trimethylammonio)phenyl)azo]-pyrazol-5-one chloride (CI 12719; Basic Yellow No. 57), bis-[4-methylamino)-phenyl]-phenylcarbenium hydrogen sulfate (1:1) (CI 42040; Basic Green No. 1), 1-[di(2-hydroxyethyl)amino]-3-methyl-4-[(4-nitro-phenyl)azo]benzene (CI 11210, Disperse Red No. 17), 4-[(4-aminophenyl)azo]-1-[di(2-hydroxyethyl)amino]-3-methyl benzene (HC Yellow No. 7), 2,6-diamino-3-[(pyridine-3yl)azo]-pyridine, 6-hydroxy-5-[(4-sulfophenyl) azo]-2-naphthalene sulfonic acid disodium salt (CI 15985; Food Yellow No. 3; FD&C Yellow No. 6), 2,4-dinitro-1-naphthol-7-sulfonic acid disodium salt (CI 10316; Acid Yellow No. 1; Food Yellow No. 1), 2-(indan-1,3-dion-2-yl) quinolin-x,x-sulfonic acid (mixture of mono and disulfonic acids) (CI 47005; D&C Yellow No. 10; Food Yellow No. 13; Acid Yellow No. 3), 5-hydroxy-1-(4-sulfo-phenyl)-4-[(4-sulfophenyl)azo]pyrazol-3-carboxylic acid trisodium salt (CI 19140; Food Yellow No. 4; Acid Yellow No. 23), 9-(2-carboxyphenyl)-6-hydroxy-3H-xanthen-3-one (CI 45350; Acid Yellow No. 73; D&C Yellow No. 8), 5-[(2,4-dinitrophenyl)amino]-2-phenylaminobenzene sulfonic acid sodium salt (CI 10385; Acid Orange No. 3), 4-[(2,4-dihydroxyphenyl)azo]-benzene sulfonic acid monosodium salt (CI 14270; Acid orange No. 6), 4-[(2-hydroxynaphth-1-yl)azo]benzene sulfonic acid sodium salt (CI 15510; Acid orange No. 7), 4-[(2,4-dihydroxy-3-[(2,4-dimethylphenyl) azo]phenyl)azo]benzene sulfonic acid sodium salt (CI 20170; Acid Orange No. 24), 4-hydroxy-3-[(4-sulfonaphth-1-yl)azo]-1-naphthalene sulfonic acid disodium salt (CI 14720; Acid Red No. 14), 6-hydroxy-5-[(4-sulfo-naphthlyl) azo]-2,4-naphthalene disulfonic acid trisodium salt (CI 16255; Ponceau 4R; Acid Red No. 18), 3-hydroxy-4-[(4-sulfonaphth-1-yl)azo]-2,7-naphthalene disulfonic acid trisodium salt (CI 16185; Acid Red No. 27), 8-amino-1-hydroxy-2-(phenylazo)-3,6-naphthalene disulfonic acid disodium salt (CI 17200; Acid Red No. 33), 5-(acetylamino)-4-hydroxy-3-(2-methylphenyl)azo]-2,7-naphthalene sulfonic acid disodium salt (CI 18065; Acid Red No. 35), 2-(3hydroxy-2,4,5,7-tetraiododibenzopyran-6-one-9-yl)benzoic acid disodium salt (CI 45430; Acid Red No. 51), N-[6-(diethylamino)-9-(2,4-disulfophenyl)-3H-xanthen-3-ylidene]-N-ethylethaneammonium hydroxide, inner salt, sodium salt (CI 45100; Acid Red No. 52), 8-[(4-(phenylazo)phenyl) azo]-7-naphthol-1,3-disulfonic acid disodium salt (CI 27290; Acid Red No. 73), 2',4',5',7'-tetrabromo-3',6'-dihydroxyspiro[isobenzofuran-1 (3H),9'-[9H]xanthene]-3-one disodium salt (CI 45380; Acid Red No. 87), 2',4',5',7'-tetrabromo-4,5,6,7-tetrachloro-3',6'-dihydroxy-spiro [isobenzofuran-1(3H),9'[9H]xanthen]-3-one disodium salt (CI 45410; Acid Red No. 92), 3',6'-dihydroxy-4',5'-diiodo-spiro[isobenzofuran-1(3H),9'(9H)xanthen]-3-one disodium salt (CI 45425; Acid Red No. 95), (2-sulfophenyl)di[4-(ethyl ((4-sulfophenyl)methyl)amino)phenyl]carbenium disodium salt, betaine (CI 42090; Acid Blue No. 9; FD&C Blue No. 1), 1,4-bis-[(2-sulfo-4-methylphenyl)amino]-9,10-anthraquinone disodium salt (CI 61570; Acid Green No. 25), bis[4-(dimethylamino)-phenyl]-(3,7-disulfo-2-hydroxynaphth-1-yl)carbenium, inner salt, monosodium salt (CI 44090; Food Green No. 4; Acid Green No. 50), bis[4-(diethylamino)phenyl]-(2,4disulfophenyl)carbenium inner salt, sodium salt (2:1) (CI 42045; Food Blue No. 3; Acid Blue No. 1), bis-[4-(diethylamino)phenyl](5-hydroxy-2,4-disulfophenyl)carbenium inner salt, calcium salt (2:1) (CI 42051; Acid Blue No. 3), 1-amino-4-(cyclohexyl-amino)-9,10-anthraquinone-2-sulfonic acid sodium salt (CI 62045; Acid Blue No. 62), 2-(1,3-dihydro-3-oxo-5-sulfo-2H-indol-2-yliden)-2,3-dihydro-3-oxo-1H-indol-5-sulfonic acid disodium salt (CI 73015; Acid Blue No. 74), 9-(2-carboxyphenyl)-3-[(2-methylphenyl)amino]-6-[(2-methyl-4-sulfophenyl)- amino]xanthylium inner salt, monosodium salt (CI 45190; Acid Violet No. 9), 1-hydroxy-4-[(4-methyl-2-sulfophenyl)amino]-9,10-anthraquinone sodium salt (CI 60730; D&C Violet No. 2; Acid Violet No. 43), bis-[3-nitro-4-[(4-phenylamino)-3-sulfophenylamino]-phenyl]-sulfone (CI 10410; Acid Brown No. 13), 5-amino-4-hydroxy-6-[(4-nitrophenyl)azo]-3-(phenylazo)-2,7-naphthalene disulfonic Acid disodium salt (CI 20470; Acid Black No. 1), 3-hydroxy-4-[(2-hydroxynaphth-1-yl)azo]-7-nitro-1-naphthalene sulfonic acid chromium complex (3:2) (CI 15711; Acid Black No. 52), 3-[(2,4-dimethyl-5-sulfophenyl) azo]-4hydroxy-1-naphthalene sulfonic acid sodium salt (CI 14700; Food Red No. 1; Ponceau SX; FD&C Red No. 4), 4-(acetylamino)-5-hydroxy-6-[(7-sulfo-4-[(4-sulfophenyl)azo]naphth-1-yl)azo]-1,7-naphthalene disulfonic acid tetrasodium salt (CI 28440; Food Black No. 1) and 3-hydroxy-4-(3-methyl-5-oxo-1-phenyl-4,5-dihydro-1H-pyrazol-4-yl-azo)-naphthalen-1-sulfonic acid sodium salt, chromium complex (Acid Red No. 195), especially 2,6-diamino-3-(pyridine-3-yl)azo-pyridine, 8-amino-2-bromo-5-hydroxy-4-imino-6-[(3-(trimethylammonio) phenyl)-amino]-1(4H)-naphthalenone chloride (CI 56059; Basic Blue No. 99), or nitro dye compounds, for example 1,4-bis-[(2-hydroxyethyl)amino]-2-nitro-benzene, 1-(2-hydroxyethyl)amino-2-nitro-4-[di(2-hydroxyethyl)-amino] benzene (HC Blue No. 2), 1-amino-3-methyl-4-[(2-hydroxyethyl)amino]-6-nitrobenzene (HC Violet No. 1), 4-[ethyl(2-hydroxyethyl)amino]-1-[(2-hydroxyethyl) amino]-2-nitrobenzene hydrochloride (HC Blue No. 12), 4-[di-(2-hydroxyethyl)amino]-1-[(2-methoxyethyl)amino]-

2-nitrobenzene (HC Blue No. 11), 1-[(2,3-dihydroxypropyl) amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethylamino-benzoic acid (HC Blue No. 13), 1-amino-4-[(2-hydroxyethyl)amino]-2-nitrobenzene (HC Red No. 7), 2-amino-4,6-dinitro-phenol, 4-amino2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitro-benzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl) amino]2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino] benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene-hydrochloride (HC Yellow No. 9), 1-[(2-ureidoethyl)amino]-4-nitrobenzene, 4-[(2,3-dihydroxypropyl)amino]-3-nitro-1-trifluoro methylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15). The following direct-dyeing dye compounds are particularly preferred for use in the oxidative dye composition of the invention: 4-amino-1-[(2-hydroxyethyl)amino]-2-nitrobenzene (HC Red No. 3), 1-amino-4-[di(2-hydroxyethyl)aminol-2-nitrobenzene hydrochloride (HC Red No. 13), 8-amino-2-bromo-5-hydroxy-4-imino-6-[(3-(trimethylammonio)phenyl)amino]-1(4H)-naphthalenone chloride (CI 56059; Basic Blue No. 99), 4-[ethyl(2-hydroxyethyl)amino]-1-[(2-hydroxyethyl)amino]-2-nitrobenzene hydrochloride (HC Blue No. 12), 1-(2-hydroxyethyl)-amino-2-nitro-4-[di(2-hydroxyethyl)amino] benzene, 4-[ethyl-(2-hydroxyethyl)amino]-1-[(2-hydroxyethyl)amino]-2-nitrobenzene hydrochloride, 4-amino-3-nitrophenol, 1-amino-4-[di(2-hydroxyethyl)amino]-2-nitrobenzene hydrochloride and/or 2-amino-6-chloro-4-nitro-phenol as well as 2,6-diamino-3-(pyridine-3-yl)azopyridine.

The direct-dyeing dye compounds can be contained in the dye carrier in amounts from about 0.1 to 10 percent by weight, preferably 0.1 to 5 percent by weight.

The dye carrier is contained in the multi-part kit separately from the oxidizing agent. The amount of hydrogen peroxide, hydrogen peroxide addition products or oxidizing enzyme contained in the multi-part kit is that which is sufficient to react the mixture of dye precursor compounds in the dye carrier quantitatively to form the dyeing agent. The oxidizing agent can either be present in ready-to-use form or as a dry substance that can be used after a subsequent addition to a suitable solution.

Usually hydrogen peroxide or its addition compounds with urea, melamine or sodium bromate can be used as the oxidizing agent contained in the multi-component kit according to the invention. Hydrogen peroxide is particularly preferred. Generally a 1 to 12 percent by weight solution of hydrogen peroxide or the hydrogen peroxide addition products is used for oxidation of the precursor compounds.

The enzymatic oxidation of the dye precursor compounds with the help of air or oxygen is however an especially careful and safe method of oxidation that can be performed under especially mild conditions. The pH in this method is in the weakly acidic or weakly basic range and the enzymatic proteins used do not attack the hair structure. In contrast to the situation when peroxide is used as the oxidizing agent however a coloring and simultaneous brightening of the hair is not possible using the enzymes with oxidizing action.

Single stage or multi-stage enzymatic oxidation systems are available for oxidative production of dye colors with the help of air or oxygen in the presence of the enzymes. In the single stage enzyme systems aromatic phenols and amines can be oxidized directly to polymeric dyestuffs in a dye mixture with oxygen addition without peroxide addition. Phenol oxidases, preferably laccases, are suitable as the enzymes. In contrast several enzymes are required for the dye production in the multi-stage enzymatic oxidation systems.

A combination of oxygen oxido-reductase/substrate systems and a peroxidase can be used for a multi-stage, enzymatic oxidation system for making the oxidation dye compound from the dye precursor compounds. For example, the following oxido-reductase/substrate systems can be used:

Glucose oxidase (EC 1.1.3.4)/D-glucose
Alcohol oxidase (EC 1.1.3.13)/ethanol
Pyruvate oxidase (EC 1.2.3.3)pyruvate
Oxalate oxidase (EC 1.2.3.4)/oxalate
Cholesterol oxidase (EC 1.1.3.6)/cholesterol
Uricase (EC 1.7.3.3)/uric acid
Lactate oxidase/lactic acid
Xanthine oxidase (EC 1.1.3.22)/xanthine.

The classification numbers occurring in the parentheses for the enzymes are according to the "Classification of the International Union of Biochemistry on Nomenclature and Classification of Enzymes", (1984).

The dye carrier and the ready-to-use dyeing composition can for example be a solution, especially an aqueous or aqueous/alcoholic solution. The preferred form of the dye carrier preparation is however a cream, a gel or an emulsion. Their composition is a mixture of dye ingredients with conventional additives used in preparations of this type. The non-oxidative dye composition contained in the multi-component kit according to the invention contains the above-named direct-dyeing dye compounds. These direct dyes are contained in the non-oxidative dye compound in an amount of from about 0.01 to 10 percent by weight, preferably from 0.1 to 5 percent by weight.

The non-oxidative dye composition can be present in the form of a solution, especially an aqueous or aqueous-alcoholic solution. The especially preferred preparation form includes however a cream, a gel an aerosol foam or an emulsion. Its composition is a mixture of dye ingredients with standard cosmetic additives suitable for this type of preparation.

Standard additive ingredients commonly used in the oxidative or non-oxidative dye composition in the form of a solution, cream, emulsions, gels or aerosol foams are, for example, solvents, such as water, low aliphatic alcohols, especially ethanol, n-propanol and isopropanol or glycols, such as glycerol and 1,2-propanediol; wetting agents or emulsifiers from the classes of anionic, cationic, amphoteric or nonionic surface-active substances, such as fatty alcohol sulfates, ethoxylated fatty alcohol sulfates, alkyl sulfonates, alkylbenzenesulfonates, alkyltrimethyl ammonium salts, alkylbetaines, ethoxylated fatty alcohols, ethoxylated nonyl phenols, fatty acid alkanol amides, ethoxylated fatty alcohols, ethoxylated nonylphenols, fatty acid alkanol amides, ethoxylated fatty acid esters; thickeners, such as higher fatty alcohols, starches or cellulose derivative compounds; perfumes, hair treatment agents, conditioners, hair swelling agents, preservatives, petrolatum(Vaseline®), paraffin oil and fatty acids as well as care materials, such as cationic resin, lanolin derivative compounds, cholesterol, pantothenic acids and betaines. The above-mentioned ingredients are used in standard amounts suitable for their purposes, for example the wetting agents and emulsifiers are used in concentrations of from about 0.5 to about 30 percent by weight (based on the total amount of the dye carrier), the thickeners are used in an amount of about 0.1 to about 25 percent by weight (based on the dye carrier) and the care substances are used in a concentration of from about 0.1 to about 5.0 percent by weight (based on the dye carrier).

The pH of the ready-to-use oxidative or non-oxidative dyeing agent amounts to from 3 to 11 usually, preferably from 5 to 9. The pH of the ready-to-use oxidation dyeing composition produced by mixing the preferably alkaline dye carrier with the mostly acidic oxidizing agent is determined by the amount of alkali in the dye carrier and the amount of acid in the oxidizing agent as well as the mixture proportions. For adjustment of the pH value of the dyeing composition alkalizing agents, such as alkanol amines, alkylamines, alkali hydroxides or ammonium hydroxides and alkali carbonates or ammonium carbonates, preferably ammonium hydroxides, or acids, such as lactic acid, acetic acid, tartaric acid, phosphoric acid, hydrochloric acid, citric acid, ascorbic acid and boric acid.

A buffer system is recommend to control the pH, particularly for the enzymatically-catalyzed oxidation. Citrate buffers, phosphate buffers or borate buffers can be used. The use of borate buffers (boric acid/NaOH) or a phosphate buffer ($KH_2PO_4/K_2HPO_4$).

In the case of oxidative dyeing methods immediately prior to use one of the above-described oxidizing agents is mixed with the dye carrier including the dye precursor compounds and direct-dyeing dye compounds, as needed, and the additive ingredients and the mixture is applied to the hair. According to the desired color depth or coverage this mixture is allowed to act for 5 to 60 minutes, preferably 15 to 30 minutes, at a temperature of from 20 to 50° C., especially from 30 to 40° C. Subsequently the hair is washed with a shampoo if necessary and rinsed with water.

The dye carrier and the oxidizing agent should be mixed with each other in a weight ratio of 5:1 to 1:3, however a weight ratio in the range from 1:1 to 1:2 is especially preferred.

In the case of non-oxidative dyeing the dye carrier including the direct-dyeing dye compounds is applied directly to the hair. According to the desired color depth or color coverage the dye carrier is allowed to act on the hair for 5 to 60 minutes, preferably 15 to 30 minutes, at a temperature of from 20 to 50° C., especially from 30 to 40° C. Subsequently the hair is washed with a shampoo if necessary and rinsed with water.

Part (II) of the multi-part kit according to the invention includes the agent for reductive decolorizing of the fibers dyed with oxidation dyestuffs and/or direct-dyeing dyestuffs as its essential ingredient. The agent for reductive decolorizing includes the combination of a) at least one reductone and/or at least one thiol compound and/or at least one sulfite compound and b) at least one α-oxocarboxylic acid or its physiologically compatible salt.

The reductone can be, for example, ascorbic acid or isoascorbic acid or their salts or esters, for example 6-O-palmitoyl ascorbate, hydroxypropaniol(triose reductone), 2,3-dihydroxy-2-cyclopenten-1-one (reductic acid) or mixture of these compounds, preferably in an amount of from 1 to 50 percent by weight, especially preferably in an amount of from 2 to 10 percent by weight. Ascorbic acid or isoascorbic acid are particularly preferred. The free acids can also be made in situ by reacting an acid with an alkali metal ascorbate or isoascorbate or with an alkaline earth metal ascorbate or isoascorbate. This latter method is advantageous because of the improved solubility of the salt in water, especially at higher concentrations. Calcium salts, magnesium salts and sodium salts of ascorbic acid or isoascorbic acid are especially suitable as salts of ascorbic or isoascorbic acid for use in the compositions and methods of the invention. Cysteine or its salts, N-acetylcysteine, cysteamine or its salts, mercaptoacetaldehyde, penicillamine, glutathione, homocysteine or its salts and/or calcium thioglycolate can be used as the thiol compound or compounds. Cysteine and its salts are especially preferred.

The decolorizing agent can also contain a sulfite compound, for example an alkali sulfite compound or an alkaline earth sulfite compound, especially sodium sulfite, in order to prevent a reverse oxidation of the dye precursor compounds remaining in the hair.

The thio compounds can be used in an amount of from 0.1 to 10 percent by weight, preferably from 2 to 5 percent by weight, while the sulfite compounds can be used in an amount of from 0.001 to 5 percent by weight, preferably in an amount of from 0.01 to 0.5 percent by weight.

Both α-ketocarboxylic acids and α-aldehyde acids, for example glyoxylic acid, pyruvic acid, oxalacetic acid or α-ketoglutaric acid, or their alkali metal or alkaline earth metal salts, can be used as the α-oxocarboxylic acid.

The α-oxocarboxylic acid or its physiologically compatible salt can be used in an amount of from 0.1 to 10 percent by weight, however use of 0.5 to 5 percent by weight is particularly preferred.

The corresponding α-oxocarboxylic acid ester does not improve the decolorizing reaction and can thus only be used after an ester soaponification as the α-oxo-carboxylic acid.

In a preferred embodiment of the invention the decolorizing composition contains as ingredient a) a combination of at least one reductone, preferably ascorbic acid, and at least one thiol compound, preferably cysteine and/or cysteine hydrochloride, and as ingredient b) an α-oxocarboxylic acid or its physiologically compatible salt.

However it is also possible to employ a decolorizing agent that contains as ingredient a) a reductone or a thiol compound or a sulfite compound alone, or a combination of a thiol compound and a sulfite compound or a combination of a reductone and a sulfite compound, or a reductone and a thiol compound and a sulfite compound, and as ingredient b) an α-oxocarboxylic acid or its physiologically compatible salt.

The composition for reductive decolorizing of the fibers dyed with a combination of oxidative dyestuffs and/or direct-dyeing dye compounds (in the following designated the "decolorizing composition") can be in the form of an aqueous or aqueous-alcoholic solution, a gel, a cream, an emulsion or a foam, and the decolorizing composition can be packaged in the form of a multi-component preparation. A solid decolorizing agent can be provided in the form of tablets, such as bath tablets, or of in the form of a granulate to protect against dust formation, as well as in the form of a powder. The decolorizing composition can be made immediately prior to use by adding the solid decolorizing agent to cold or warm water, together with one or more subsequently-named auxiliary materials as needed. However it is also possible to provide the auxiliary materials (when they are solids) in the decolorizing powder or granulate. Dust formation can be avoided by moistening the power with oil or wax.

The decolorizing composition can of course contain additional auxiliary ingredients, for example, solvents, such as water, lower aliphatic alcohols, for example ethanol, n-propanol and isopropanol, glycol ether or glycols, such as glycerol, and especially 1,2-propandiol; wetting agents or emulsifiers from the classes of anionic, cationic, amphoteric or nonionic surface-active substances, such as fatty alcohol sulfate, ethoxylated fatty alcohol sulfates, alkylsulfonates, alkyl benzene sulfonates, alkyltrimethylammonium salts, alkyl betaines, ethoxylated fatty alcohols, ethoxylated nonyl phenols, fatty acid alkanol amides, ethoxylated fatty alcohols, ethoxylated nonylphenols, fatty acid alkanol amides, ethoxylated fatty acid esters; thickeners, such as higher fatty alcohols, starches or cellulose compounds, perfumes, hair treatment agents, conditioners, hair swelling agents, preservative materials, petrolatum (Vaseline®), paraffin oil and fatty acids as well as additionally care substances, such as cationic resins, lanolin derivative compounds, cholesterol, pantothenic acid and betaine.

The pH values of the decolorizing composition should be about 1.8 to 6, preferably 2.5 to 4. In case it is necessary the desired pH can be obtained by addition of additional acids, for example α-hydroxycarboxylic acids, such as lactic acid, tartaric acid, citric acid or malic acid, phosphoric acid, acetic acid, glycolic acid, salicylic acid, glutathione or gluconic acid lactone, or also by addition of alkanol amines, alkyl amines, alkali hydroxides, ammonium hydroxides, alkali carbonates, ammonium carbonates or alkali phosphates.

Although it is especially easy to add the α-oxocarboxylic acid directly to the decolorizing composition it is similarly possible to obtain the desired decolorizing results without impairment by packaging the α-oxocarboxylic acid separately from the decolorizing composition and by using the α-oxo-carboxylic acid subsequently to the decolorizing composition in a special after-treatment.

It is similarly possible to simultaneously provide the α-oxocarboxylic acid or its physiologically compatible salt in both the decolorizing composition and also in an after-treatment composition.

It was surprisingly found that the decolorizing results were nearly the same immediately after the breaching treatment both without the α-oxocarboxylic acid and also with α-oxocarboxylic acid; after a few minutes however distinct differences in the two treatments appeared. The hair decolorizing without α-oxo-carboxylic acid thus appeared partially colored after a few hours or days because of air oxidation, while the hair bleached with α-oxocarboxylic acid remained unchanged. The α-oxo-carboxylic acid causes thus both a fixing of the decolorizing results and prevents a reversal of the decolorizing process.

The acting time of the decolorizing composition amounts to from 5 to 60 minutes, especially 15 to 30 minutes, according to the dye to be bleached and the temperature (about 20 to 50° C.). Application of heat will of course accelerate the decolorizing process. After the time interval required for decolorizing the hair is rinsed with water and if necessary washed with a shampoo composition.

If the decolorizing agent contains no α-oxocarboxylic acid, the hair is rinsed with an α-oxocarboxylic acid containing rinse, preferably having an acidic pH, and then dried.

The use of the decolorizing composition according to the invention of part (II) of course does not need to be limited to decolorizing colors of hair dyed with the part (I) of the multi-part kit according to the invention. Furthermore the decolorizing preparation of part (II) can be used entirely by itself for decolorizing of colors produced by the hair dyeing composition of part (I) and also in other and independent ways. Furthermore the decolorizing preparation of part (II) is also suitable for decolorizing many natural or synthetic fibers, such as cotton, silk, viscose rayon, nylon, cellulose acetate, in so far as they have been dyed with oxidation dyestuffs or direct-dyeing dye compounds, and it is not limited to decolorizing only keratin fibers, for example wool, fur or human hair.

The subject matter of the present invention thus also includes a composition for reductive decolorizing of fibers, especially hair, dyed with oxidative dyestuffs and/or direct-dyeing dye compounds, a combination of at least one reductone, for example ascorbic acid or isoascorbic acid, or their salts or esters, for example 6-O-palmitoyl ascorbic acid, hydroxypropandiol (triose reductone), 2,3-dihydroxy-2-cyclopenten-1-one (reductic acid) or mixtures thereof, preferably with ascorbic acid; and/or at least one thiol compound, especially cysteine or its salts, and/or at least one sulfite compound, especially sodium sulfite, and at least one α-oxocarboxylic acid or a physiologically compatible salt thereof.

The subject matter of the invention also includes a method for decolorizing fibers, especially hair, dyed with oxidative dyeing agents and/or direct-dyeing dye stuffs, using a combination of at least one reductone, for example ascorbic acid or isoascorbic acid or their salts; and at least one thiol compound, especially cysteine or its salts, and at least one α-oxocarboxylic acid or a physiologically compatible salt thereof.

The decolorizing agent according to the invention provides a rapid, safe, uniform and maintainable decolorizing of fibers dyed by oxidative dyestuffs and/or direct-dyeing dye stuffs.

The subsequent examples should illustrate the subject matter of the invention without limiting the broad concept of the invention according to the appended claims.

EXAMPLES

Examples 1.1 to 1.14:
a. Oxidation hair dye composition

| | |
|---|---|
| Developer substance(s) (if necessary mixed with NH$_3$(25% aqueous solution) or NaOH (10% aqueous solution) | Amounts from Table I |
| Coupler substance(2) (if necessary mixed with NH$_3$(25% aqueous solution) or NaOH (10% aqueous solution) | Amounts from Table I |
| Nitro dye compounds | Amounts From Table I |
| Disodium ethylenediamine tetracetate | 0.30 g |
| Sodium sulfite | 0.40 g |
| Sodium lauryl ether sulfate (28% aqueous solution) | 10.00 g |
| isopropanol | 10.00 g |
| ammonia(25% aqueous solution) | 9.10 g |
| water, desalenated | to 100.00 g |

5 g of the above dye carrier was mixed with 5 g of 4% hydrogen peroxide solution. The ready-to-use oxidation hair dye composition obtained by the mixing is applied to hair and distributed uniformly with a brush. After an acting time of 30 minutes at 40° C. the hair is rinsed with lukewarm water and then dried.

B1. Decolorizing Gel:

| | |
|---|---|
| Ascorbic acid | 5.00 g |
| Methylhydroxyethylcellulose (Tylose MHB 10,000P of Hoechst, Germany) | 1.50 g |
| Cysteine | 2.00 g |
| Glyoxylic acid | 0.50 g |
| Trisodium citrate dihydrate | 0.30 g |
| Water | to 100.00 g |

B2: Decolorizing Gel:

| | |
|---|---|
| Isoascorbic acid | 5.00 g |
| Methylhydroxyethylcellulose (Tylose MHB 10,000P of Hoechst, Germany) | 1.50 g |
| Cysteine | 2.00 g |
| Sodium sulfite | 0.05 g |
| Glyoxylic acid | 0.50 g |
| Trisodium citrate dihydrate | 0.20 g |
| Water | to 100.00 g |

B3. Decolorizing Gel:

| | |
|---|---|
| Ascorbic acid | 10.00 g |
| Hydroxyethylcellulose | 1.50 g |
| Glutathione | 1.00 g |
| Glyoxylic acid | 0.50 g |
| Trisodium citrate dihydrate | 0.90 g |
| Water | to 100.00 g |

B4. Decolorizing Gel:

| | |
|---|---|
| Sodium ascorbate | 6.00 g |
| Citric acid | 6.00 g |
| Hydroxyethylcellulose | 1.50 g |
| Glyoxylic acid | 0.50 g |
| Water | to 100.00 g |

B5. Decolorizing Gel:

| | |
|---|---|
| Isoascorbic acid | 6.00 g |
| Methylhydroxyethylcellulose (Tylose MHB 10,000P of Hoechst, Germany) | 1.50 g |
| Cysteine | 2.00 g |
| α-Ketoglutaric acid | 0.80 g |
| Water | to 100.00 g |

The pH is adjusted with trisodium citrate dihydrate to from 2.5 to 3.0.

B6. Decolorizing Gel:

| | |
|---|---|
| Sodium ascorbate | 5.70 g |
| L-Cysteine | 2.00 g |
| Magnesium sulfate | 1.00 g |
| Citric acid | 7.40 g |
| Trisodium citrate dihydrate | 1.00 g |
| Hydroxyethylcellulose | 1.50 g |
| 2-oxoglutaric acid | 0.80 g |
| Water | to 100.00 g |

B7. Decolorizing Gel:

| | |
|---|---|
| Sodium ascorbate | 5.70 g |
| L-Cysteine | 2.00 g |
| Magnesium sulfate | 1.00 g |
| Citric acid | 7.40 g |
| Trisodium citrate dihydrate | 0.60 g |
| Hydroxyethylcellulose | 1.50 g |
| Glyoxylic acid | 0.50 g |
| Water | to 100.00 g |

B8. Decolorizing Gel:

| | |
|---|---|
| Sodium ascorbate | 5.70 g |
| L-Cysteine | 2.00 g |
| Magnesium sulfate | 1.00 g |
| Citric acid | 7.40 g |
| Trisodiuin citrate dihydrate | 1.00 g |
| Hydroxyethylcellulose | 1.50 g |
| Oxalacetic acid | 0.70 g |
| Water | to 100.00 g |

The above-described decolorizing gels are applied to the dyed hair and allowed to remain on it for 30 minutes at 37° C. in the case of the decolorizing gels B1 to B3, for 60 minutes at 40° C. in the case of the decolorizing gels B4 to B5 and from 20 to 60 minutes at 30° C. in the case of the decolorizing gel B6 under a plastic cover. After that the hair is rinsed with water and washed with a shampoo then rinsed again with water as needed and dried.

The results of the exemplary decolorizing treatments are summarized in Table I hereinbelow.

TABLE I

DYEING AND DECOLORIZING RESULTS

| No. | Developer/ Coupler Combination | Color Shade After dyeing | Measured Color Values | | | Bleach % |
|---|---|---|---|---|---|---|
| | | | L | a | b | |
| 1.1 | 0.62 g, 1,4-diamino-2-(2-hydroxyethyl)-benzene sulfate 0.55 g, 1,4-diamino-2-methylbenzene sulfate | deep violet | untreated hair: 37.29; after dyeing 25.24; | 8.13; 12.32; | 15.88 3.35 | |

TABLE I-continued

DYEING AND DECOLORIZING RESULTS

| No. | Developer/ Coupler Combination | Color Shade After dyeing | Measured Color Values L a b | | | Bleach % |
|---|---|---|---|---|---|---|
| | 0.61 g, 5-amino-2-methylphenol | | after 1x decolorizing with B2: 35.95; | 9.42; | 14.42 | 87 |
| 1.2 | 1.05 g, 4-diamino-2-(aminomethyl)-phenol hydrochloride 0.61 g, 5-amino-2-methylphenol sulfate | orange | untreated hair: 37.29; after dyeing 30.22; | 8.13; 14.32; | 15.88 14.00 | |
| | | | after 1x decolorizing with B1: 37.57; | 9.35; | 16.71 | 84 |
| 1.3 | 0.61 g, 4-amino-3-methyl-phenol 0.36 g 1-naphthol 0.31 g, 5-amino-2-methyl-phenol 0.5 g, 4-[ethyl-(2-hydroxyethyl)-amino]-1-[2-(2-hydroxyethyl)-amino]-2-nitrobenzene hydrochloride (HC Blue No. 12) | violet after dyeing 30.42; | untreated hair: 37.29; 10.41; | 8.13; 7.99 | 15.88 | |
| | | | after 1x decolorizing with B1: 37.72; | 9.30; | 14.26 | 81 |
| 1.4 | 1.92 g, 4-amino-3-methyl-phenol 0.32 g 1-naphthol 0.61 g, 2-amino-4-[(2-hydroxy-ethyl)amino)-anisole sulfate 1.38g, 5-amino-2-methyl-phenol 1.00 g,HC Blue No. 12 | blue-violet | untreated hair: 34.41; after dyeing 22.82; | 7.27; 6.86; | 13.78 3.87 | |
| | | | after 1x decolorizing with B3: 35.38; | 8.95; | 12.92 | 86 |
| 1.5 | 2.2 g, 1,4-diamino-2-methylbenzene sulfate 1.23 g, 5-amino-2-methylphenol | deep violet | untreated hair: 34.41; after dyeing 20.04; | 7.27; 7.55; | 13.78 0.08 | |
| | | | after 1x decolorizing with B4(40° C.,60 min): 31.85; | 9.28; | 14.54 | 83 |
| 1.6 | 1.2 g, 4,5-diamino-1-(2-hydroxyethyl)-1H-pyrazole 0.62 g, 5-amino-2-methylphenol | intense orange-red | untreated hair: 34.41; after dyeing 27.66; | 7.27; 23.98; | 13.78 15.06 | |
| | | | after 1x decolorizing with B4(40° C., 60 min): 33.83; | 10.92; | 15.08 | 78 |
| 1.7 | 1.25, 1,4-diamino-2-(2-hydroxyethyl)-benzene sulfate 1.20 g, 4-(2-hydroxyethoxy)-1,3-phenylenediamine dihydrochloride | blue-black | untreated hair: 34.41; after dyeing 19.76; | 7.27; 0.70; | 13.78 −2.15 | |
| | | | after 1x decolorizing with B4(40° C., 60 min): 32.21; | 10.31; | 12.98 | 83 |
| 1.8 | 1.92g, 4-amino-3-methyl-phenol 0.32 g 1-naphthol 0.61 g, 2-amino-4-[(2-hydroxy-ethyl)amino]-anisole sulfate 1.38 g, 5-amino-2-methyl-phenol | red-brown | untreated hair: 34.41; after dyeing 28.18; | 7.27; 15.19; | 13.78 11.12 | |
| | | | after 1x decolorizing with B4(40° C., 60 min): 34.65; | 9.63; | 14.76 | 75 |
| 1.9 | 0.55 g, 1,4-diamino-2-methylbenzene sulfate 0.31 g, 5-amino-2-methylphenol 0.5 g, 2-methyl-1-naphthol acetate | deep violet | untreated hair: 34.41; after dyeing 20.74; after 1x decolorizing | 7.27; 7.91; | 13.78 −0.53 | 90 |

TABLE I-continued

DYEING AND DECOLORIZING RESULTS

| No. | Developer/ Coupler Combination | Color Shade After dyeing | Measured Color Values L a b | | | Bleach % |
|---|---|---|---|---|---|---|
| 1.10 | 1.2g, 1,4-diamino-2-hydroxyethyl-benzene sulfate 1.0 g, 5-((2,2,2-trifluoro-ethyl)amino)-2-methyl-phenol | violet | with B4(40° C., 60 min): 35.20; 9.05; 14.40 untreated hair: 84.20; −1.36; 8.81 after dyeing 25.22; 18.36; −4.83 after 1x decolorizing with B4(40° C., 60 min): 70.83; 9.59; 19.81 | | | 69 |
| 1.11 | 0.55 g, 1,4-diamino-2-methylbenzene sulfate 0.6 g, 4,5-diamino-1-(2-hydroxyethyl)-1H-pyrazole 0.62 g, 5-amino-2-methylphenol | intense red — | untreated hair: 34.41; 7.27; 13.78 after dyeing 21.13; 14.99; 5.29 after 1x decolorizing with B4(40° C., 60 min): 35.65; 10.35; 16.84 | | | 74 |
| 1.12 | 1.10 g, 1,4-diamino-2-methylbenzene sulfate 1.25 g, 1,4-diamino-2-(2-hydroxyethyl)-benzene sulfate 0.25 g, 5-amino-2-methylphenol 1.74 g, 1,3-Di(2,4-diaminophenoxy)-propane | blue-black 33.5; | untreated hair: 31.9; 7.0; 11.7 after dyeing 20.4; 0.8; −1.3 after 1x decolorizing with B6: 9.0; 13.2 | | | 84 |
| 1.13 | 1.10 g, 1,4-diamino-2-methylbenzene sulfate 1.25 g, 1,4-diamino-2-(2-hydroxyethyl)-benzene sulfate 0.25 g, 5-amino-2-methylphenol 1.74 g, 1,3-Di(2,4-diaminophenoxy)-propane | blue-black | untreated hair: 32.1; 6.7; 11.2 after dyeing 18.9; 0.6; −1.1 after 1x decolorizing with B7: 33.9; 8.0; 11.1 | | | 89 |
| 1.14 | 1.10 g, 1,4-diamino-2-methylbenzene sulfate 1.25 g, 1,4-diamino-2-(2-hydroxyethyl)-benzene sulfate 0.25 g, 5-amino-2-methylphenol 1.74 g, 1,3-Di(2,4-diaminophenoxy)-propane | blue-black 32.0; | untreated hair: 30.6; 6.8; 10.9 after dyeing 19.5; 0.8; −1.0 after 1x decolorizing with B8: 8.9; 12.8 | | | 82 |

EXAMPLES 2.1 to 2.7

The dyeing occurs on bleached hair in the same manner as described in Example 1(concentration of the dyestuffs: 0.05 mol/l).

The decolorizing occurs with either decolorizing composition B1 or B2.

The above-described decolorizing composition is applied to the dyed hair and allowed to act on the hair for 20 or 30 minutes respectively at 37° C. under a plastic cover, after that the hair is washed thoroughly with water and a shampoo, rinsed with water and then dried.

The results of the dyeing and decolorizing are tabulated in the following Table II.

TABLE II

DYEING AND DECOLORIZING RESULTS

| No. | Developer/Coupler Combination | Color Shade After dyeing | Decolorizing Agent/Decolorizing Time | | Color After Decolorization |
|---|---|---|---|---|---|
| 2.1 | 1,4-diamino-2-methyl-benzene sulfate<br>1,3-dihydroxybenzene | brown | B1 | 30 min | beige |
| 2.2 | 1,4-diamino-2-methyl-benzene sulfate<br>1-naphthol | dark blue | B2 | 30 min | gray |
| 2.3 | 1,4-diamino-2-methyl-benzene sulfate<br>3-amino-6-methoxy-2-(methylamino)pyridine | dark blue | B1 | 30 min | brownish |
| 2.4 | 4,5-diamino-1-(2-hydroxyethyl)1H-pyrazole<br>1-naphthol | intense red | B1 | 30 min | rose |
| 2.5 | 1,4-diamino-2-(2-hydroxyethyl)benzene sulfate<br>5-amino-2-methylphenol | intense violet | B2 | 20 min | faint yellow |
| 2.6 | 4,5-diamino-1-(2-hydroxyethyl)1H-pyrazole<br>2-amino-4-[(2-hydroxyethyl)-amino]anisole sulfate | bordeaux red | B2 | 30 min | faint bordeaux red |
| 2.7 | 4-amino-3-methyl-phenol(0.06%),<br>1-naphthol(0.04%),<br>5-amino-2-methylphenol(0.03%) | rose red | B2 | 20 min | colorless |

EXAMPLES 2.1 to 2.7

The dyeing occurs on bleached hair in the same manner as described in Example 1(concentration of the dyestuffs: 0.05 mol/l). The decolorizing takes place with the decolorizing composition B9.1.

| B9.1. Decolorizing Gel: | |
|---|---|
| Sodium ascorbate | 5.60 g |
| Methylhydroxyethylcellulose (Tylose MHB 10,000P of Hoechst, Germany) | 1.50 g |
| Cysteine hydrochloride | 2.50 g |
| Citric acid | 5.00 g |
| Water | to 100.00 g |

The above-described decolorizing agent is applied to the hair and allowed to act for on the hair for 20 or 30 minutes respectively at 37° C under a plastic cover, after that the hair is washed thoroughly with water and a shampoo, rinsed with the following glyoxylic acid-containing after-treatment composition B9.2, rinsed with water and then dried.

| B9.2 After-treatment Composition: | |
|---|---|
| Cetrimonium chloride(50%) | 1.00 g |
| Glyoxylic acid (50%) | 1.00 g |
| Hydroxyethylcellulose | 1.50 g |
| Trisodium citrate dihydrate | 0.30 g |
| Water | ad 100.00 g |

The results for the dyeing and decolorizing appear in the following Table IIa.

TABLE IIa

DYEING AND DECOLORIZING RESULTS

| No. | Developer/Coupler Combination | Color Shade After dyeing | Decolorizing Agent/Decolorizing Time | | Color After Decolorization |
|---|---|---|---|---|---|
| 2.8 | 4-amino-3-methyl-phenol<br>2-amino-4-[(2-hydroxyethyl)amino]anisole sulfate | bright violet | B9.1 & B9.2 | 30 min | faint yellow |
| 2.9 | 1,4-diamino-2-methyl-benzene sulfate<br>2-amino-4-[(2-hydroxyethyl) amino]anisole sulfate | dark blue | B9.1 & B9.2 | 30 min | faint beige |
| 2.10 | 1,4-diamino-2-methyl-benzene sulfate<br>3-aminophenol | intense gray-violet | B9.1 & B9.2 | 30 min | faint red-brown |

TABLE IIa-continued

DYEING AND DECOLORIZING RESULTS

| | | | | | |
|---|---|---|---|---|---|
| 2.11 | 1,4-diamino-2-methyl-benzene sulfate<br>5-[(2-hydroxyethyl) amino]-1,3-benzodioxol hydrochloride | green black | B9.1 & B9.2 | 30 min | green |
| 2.12 | 1,4-diamino-2-methyl-benzene sulfate<br>1,3-dihydroxy-2-methylbenzene | brown | B9.1 & B9.2 | 30 min | bright brown |
| 2.13 | 4-amino-3-methyl-phenol<br>5-amino-2-methyl-phenol | salmon | B9.1 & B9.2 | 20 min | colorless |
| 2.14 | 1,4-diamino-2-methyl-benzene sulfate<br>1,3-Di(2,4-diamino-phenoxy)propane | deep blue | B9.1 & B9.2 | 30 min | faint orange-beige |
| 2.15 | 4,5-diamino-1-(2-hydroxy-ethyl)1H-pyrazole<br>1,3-dihydroxybenzene | red | B9.1 & B9.2 | 30 min | faint rosé |
| 2.16 | 4,5-diamino-1-(2-hydroxy-ethyl)1H-pyrazole<br>3-aminophenol | red | B9.1 & B9.2 | 20 min | colorless |
| 2.17 | 4,5-diamino-1-(2-hydroxy-ethyl)1H-pyrazole<br>3-amino-6-methoxy-2-methylamino-pyridine | blue-black | B9.1 & B9.2 | 30 min | beige-gray |
| 2.18 | 4,5-diamino-1-(2-hydroxy-ethyl)1H-pyrazole<br>1,3-dihydroxy-2-methylbenzene | red | B9.1 & B9.2 | 30 min | faint rose |
| 2.19 | 4-aminophenol<br>5-amino-2-methylphenol | salmon | B9.1 & B9.2 | 20 min | colorless |
| 2.20 | 1,4-diaminobenzene<br>5-amino-2-methylphenol | violet | B9.1 & B9.2 | 30 min | faint beige |
| 2.21 | 2,4,5,6-tetraaxnino-pyrimidine sulfate<br>5-amino-2-methylphenol | blue | B9.i & B9.2 | 20 rnin | colorless |
| 2.22 | 2,5-diamino-4-methyl-phenol dihydrochloride<br>5-amino-2-methylphenol | deep-blue | B9.1 & B9.2 | 30 min | faint gray |
| 2.23 | 4-amino-3-methylphenol<br>2,4-diamino-6-methylphenol | beige | B9.1 & B9.2 | 30 min | faint yellow |
| 2.24 | 1,4-diamino-2-methyl-benzene sulfate<br>3-amino-2-methylphenol | brown | B9.1 & B9.2 | 30 min | bright brown |
| 2.25 | 4,5-diamino-1-(2-hydroxy-ethyl)1H-pyrazole<br>3-(2-hydroxyethyl)amino-phenol | intense red | B9.1 & B9.2 | 30 min | faint rosé |
| 2.26 | 4,5-diamino-1-(2-hydroxy-ethyl)1H-pyrazole<br>5-(2-hydroxyethyl)amino-2-methylphenol | intense orange | B9.1 & B9.2 | 30 min | faint orange |
| 2.27 | 4-amino-3-methylphenol<br>5-amino-2-ethylphenol | rose-orange | B9.1 & B9.2 | 20 min | colorless |
| 2.28 | 4,5-diamino-1-(2-hydroxy-ethyl)1H-pyrazole<br>2-methyl-1-naphthol acetate | intense rose | B9.1 & B9.2 | 30 min | faint rose |
| 2.29 | 1,4-diaminobenzene<br>1,3-diaminobenzene | deep-blue | B9.1 B9.2 | 30 min | beige |
| 2.30 | 1,4-diamino-2-(2-hydroxy-ethyl)benzene sulfate<br>1,3-diaminobenzene | deep-blue | B9.1 & B9.2 | 20 min | faint yellow |

| | Developer/ | Color Shade | Measured Color Values | | | Bleach |
|---|---|---|---|---|---|---|
| No. | Coupler/Combination | After dyeing | L | a | b | % |
| 2.31 | 0.44 g, 1,4-diamino-2-methylbenzene sulfate<br>0.37 g, 4-amino-3-methyl-phenol<br>0.48 g, 2,4-diamino-1-(2-hydroxyethoxy)-benzene dihydrochloride<br>0.37 g, 5-amino- | violet | untreated hair:<br>37.29; 8.13; 15.88<br><br>after dyeing<br>26.31; 4.95; 3.55<br><br>after 1x decolorizing | | | <br><br><br><br><br>79 |

TABLE IIa-continued

DYEING AND DECOLORIZING RESULTS

|  |  |  |  |  |
|---|---|---|---|---|
|  | 2-methylphenol |  | with B9.1 & B9.2:<br>39.77; 9.37; 17.90 |  |
| 2.32 | 0.22 g, 1,4-diamino-<br>2-methylbenzene sulfate<br>0.50 g, 4-amino-3-methyl-<br>phenol<br>0.61 g, 5-amino-2-methyl-<br>phenol | red | untreated hair:<br>82.29; −0.48; 10.40<br><br>after dyeing<br>47.18; 31.48; 17.32<br>after 1x decolorizing<br>with B9.1 & B9.2:<br>80.94; 0.33; 15.74 | 90 |
| 2.33 | 0.83 g, 1,4-diamino-<br>2-methylbenzene sulfate<br>0.42 g, 2-amino-4-[(2-hydroxy-<br>ethyl)amino]anisole sulfate<br>0.46 g, 4-amino-3-methyl-<br>benzene<br>0.225 g, 2-amino-6-chloro-<br>4-nitrophenol | dark<br>brown | untreated hair:<br>34.41; 7.27; 13.78<br><br>after dyeing<br>21.22; 4.66; 3.90<br>after 1x Decolorizing<br>with B9.1 & B9.2:<br>33.87; 7.53; 13.97 | 96 |

EXAMPLES 2.34 to 2.36

The dyeing occurs on bleached hair in the same manner as described in Example 1 (concentration of the dyestuffs: 0.05 mol/l).

The decolorizing takes place with the decolorizing compositions B6, B7 or B8 described in examples 1.1 to 1.14. A glyoxylic acid-containing composition according to B9.2 from examples 2.8 to 2.33 was used for the after-treatment.

The above-mentioned decolorizing agent B6, B7 or B8 was applied to the hair and allowed to act for on the hair for 30 minutes at 37° C. under a plastic cover, after that the hair was washed thoroughly with water and a shampoo, treated for five minutes the glyoxylic acid-containing after-treatment composition B9.2, rinsed with water and then dried.

The results for the dyeing and decolorizing appear in the following Table IIb.

TABLE IIb

| No. | Developer/<br>Coupler Combination | Color Shade<br>After dyeing | Measured Color Values | | | Bleach<br>% |
|---|---|---|---|---|---|---|
|  |  |  | L | a | b |  |
| 2.34 | 1.10 g, 1,4-diamino-<br>2-methylbenzene sulfate<br>1.25 g, 1,4-diamino-2-<br>(2-hydroxyethyl)-<br>benzene sulfate<br>0.25 g, 5-amino-2-methyl-<br>phenol<br>1.74 g, 1,3-Di(2,4-diamino-<br>phenoxy)propane | blue-<br>black | untreated hair:<br>31.9; 7.0; 11.7<br><br>after dyeing<br>20.4; 0.8; −1.3<br>after 1x decolorizing<br>with B6 & then 5 min after-<br>treatment with B9.2:<br>33.9; 9.0; 13.2 | | | 84 |
| 2.35 | 1.10 g, 1,4-diamino-<br>2-methylbenzene sulfate<br>1.25 g, 1,4-diamino-2-<br>(2-hydroxyethyl)-<br>benzene sulfate<br>0.25 g, 5-amino-2-methyl-<br>phenol<br>1.74 g, 1,3-Di(2,4-diamino-<br>phenoxy)propane | blue-<br>black | untreated hair:<br>32.1; 6.7; 11.2<br><br>after dyeing<br>18.9; 0.6; −1.1<br>after 1x decolorizing<br>with B6 & then 5 min after-<br>treatment with B9.2:<br>33.9; 8.0; 11.1 | | | 89 |
| 2.36 | 1.10 g, 1,4-diamino-<br>2-methylbenzene sulfate<br>1.25 g, 1,4-diamino-2-<br>(2-hydroxyethyl)-<br>benzene sulfate<br>0.25 g, 5-amino-2-methyl-<br>phenol<br>1.74 g, 1,3-Di(2,4-diamino-<br>phenoxy)propane | blue-<br>black | untreated hair:<br>30.6; 6.8; 10.9<br><br>after dyeing<br>19.5; 0.8; −1.0<br>after 1x decolorizing<br>with B6 & then 5 min after-<br>treatment with B9.2:<br>32.0; 8.9; 12.8 | | | 82 |

EXAMPLES 3.1 to 3.32

The dyeing occurs on bleached hair in the same manner as described in Example 1(concentration of the dyestuffs: 0.05 mol/l).

The decolorizing takes place with the following decolorizing compositions:

A. Bleaching Gel(corresponding to B4 of Example 1):

| | |
|---|---|
| Sodium ascorbate | 6.00 g |
| Citric acid | 6.00 g |
| Hydroxyethyl cellulose | 1.50 g |
| Glyoxylic acid | 0.50 g |
| Water | to 100.00 g |

The pH of the decolorizing agent is between 2.5 and 3.5.

B. Decolorizing Solution:

| | |
|---|---|
| Ascorbic acid | 10 g |
| Glyoxylic acid | 0.5 g |
| Water, desalenated | to 100.00 g |

C. Decolorizing Balsam:

| | |
|---|---|
| Cetylstearyl alcohol | 4.50 g |
| Cetyl lactate | 0.50 g |
| Dimethicone | 0.50 g |
| Cetyltrimethylammonium chloride | 0.65 g |
| Glyoxylic acid | 0.50 g |
| Ascorbic acid | 6.00 g |
| Water, desalenated | to 100.00 g |

The pH of the bleaching balsams is adjusted to 2.5 with a 2% aqueous NaOH solution.

D. Bleaching Foam:

| | |
|---|---|
| Cetylstearyl alcohol | 1.30 g |
| PEG-35 Castor Oil | 0.47 g |
| Cetyltrimethylammonum chloride | 0.94 g |
| Ascorbic acid | 6.00 g |
| Glycolic acid | 0.50 g |
| Water, desalenated | to 100.00 g |
| Propane/butane | 6.00 g |

The pH of the decolorizing foam is adjusted with trisodium citrate dihydrate to pH=2.5.

The hair was treated with the decolorizing composition for 20 to 60 minutes at 40° C., subsequently thoroughly washed with water and a shampoo and then dried.

The results of the dyeing and decolorizing are assembled in the following Table III.

TABLE III

DYEING AND DECOLORIZING RESULTS

| No. | Developer/ Coupler Combination | Color Shade After dyeing | Decolorizing Agent/ Decolorizing Time | Color After Decolorization |
|---|---|---|---|---|
| 3.1 | 4-amino-3-methyl-phenol 2-amino-4-[(2-hydroxy-ethyl)amino]anisole sulfate | bright violet | B/60 min | faint yellow |
| 3.2 | 1,4-diamino-2-methyl-benzene sulfate 2-amino-4-[(2-hydroxy-ethyl)amino]anisole sulfate | dark blue | B/60 min | faint gray-blue |
| 3.3 | 1,4-diamino-2-methyl-benzene sulfate 1,3-dihydroxybenzene | brown | C/45 min | bright brown |
| 3.4 | 1,4-diamino-2-methyl-benzene sulfate 3-aminophenol | intense gray-violet | C/45 min | faint red-brown |
| 3.5 | 1,4-diamino-2-methyl-benzene sulfate 1-naphthol | dark blue | C/60 min | gray |
| 3.6 | 1,4-diamino-2-methyl-benzene sulfate 3-amino-6-methoxy-2-methylaminopyridine | dark blue | A/60 min | brown |
| 3.7 | 1,4-diamino-2-methyl-benzene sulfate 5-((2-hydroxyethyl-amino)-1,3-benzodioxole-hydrochloride | green-black | C/45 min | greenish |
| 3.8 | 1,4-diamino-2-methyl-benzene sulfate 1,3-dihydroxy-2-methylbenzene | brown | C/60 min | bright brown |
| 3.9 | 4-amino-3-methyl-phenol 5-amino-2-methylphenol | salmon | D/20 min | colorless |

TABLE III-continued

DYEING AND DECOLORIZING RESULTS

| No. | Developer/ Coupler Combination | Color Shade After dyeing | Decolorizing Agent/ Decolorizing Time | Color After Decolorization |
|---|---|---|---|---|
| 3.10 | 4,5-diamino-1-(2-hydroxy-ethyl)1H-pyrazole<br>1-naphthol | intense red | B/45 min | rose |
| 3.11 | 4,5-diamino-1-(2-hydroxy-ethyl)1H-pyrazole<br>3-hydroxy-4-methoxy benzoic acid | red-orange | B/60 min | faint rose |
| 3.12 | 1,4-diamino-2-(2-hydroxy-ethyl)benzene sulfate<br>5-amino-2-methylphenol | intense violet | A/20 min | faint yellow |
| 3.13 | 4,5-diamino-1-(2-hydroxy-ethyl)1H-pyrazole<br>1,3-dihydroxybenzene | red | A/30 min | faint rose |
| 3.14 | 4,5-diamino-1-(2-hydroxy-ethyl)1H-pyrazole<br>3-aminophenol | red | A/20 min | faint beige |
| 3.15 | 4,5-diamino-1-(2-hydroxy-ethyl)1H-pyrazole<br>3-amino-6-methoxy-2-methyl-aminopyridine | blue-black | B/60 min | gray |
| 3.16 | 4,5-diamino-1-(2-hydroxy-ethyl)1H-pyrazole<br>2-amino-4-(2-hydroxy-ethyl)amino-anisole sulfate | bordeaux red | B/60 min | faint bordeaux red |
| 3.17 | 4,5-diamino-1-(2-hydroxy-ethyl)1H-pyrazole<br>1,3-dihydroxy-2-methylbenzene | red | B/60 min | faint rose |
| 3.18 | 4-aminophenol<br>5-amino-2-methylphenol | salmon | A/20 min | colorless |
| 3.19 | 1,4-diaminobenzene<br>5-amino-2-methylphenol | violet beige | A/45 min | faint |
| 3.20 | 2,4,5,6-tetraamino-pyrimidine sulfate<br>5-amino-2-methylphenol | blue | A/20 min | colorless |
| 3.21 | 2,5-diamino-4-methyl-phenol dihydrochloride<br>5-amino-2-methylphenol | deep-blue | A/60 min | faint gray |
| 3.22 | 1,4-diamino-2-hydroxy-methyl benzene sulfate<br>5-amino-2-methylphenol | beige | A/60 min | faint orange |
| 3.23 | 4-amino-3-methylphenol<br>2,4-diamino-6-methylphenol | beige | A/60 min | faint yellow |
| 3.24 | 1,4-diamino-2-methyl-benzene sulfate<br>3-amino-2-methylphenol | brown | A/60 min | bright brown |
| 3.25 | 4,5-diamino-1-(2-hydroxy-ethyl)1H-pyrazole<br>3-(2-hydroxyethyl)amino-phenol | intense red | B/60 min | faint rosé |
| 3.26 | 4,5-diamino-1-(2-hydroxy-ethyl)1H-pyrazole<br>5-(2-hydroxyethyl)amino-2-methylphenol | intense orange | B/60 min | faint orange |
| 3.27 | 4-amino-3-methylphenol<br>5-amino-2-ethylphenol | rose-orange | A/20 min | colorless |
| 3.28 | 4,5-diamino-1-(2-hydroxy-ethyl)1H-pyrazole<br>2-methyl-1-naphthol acetate | intense rose | B/60 min | faint rose |
| 3.29 | 1,4-diaminobenzene<br>1,3-diaminobenzene | deep-blue | A/60 min | beige |
| 3.30 | 1,4-diamino-2-(2-hydroxy-ethyl)benzene sulfate<br>1,3-diaminobenzene | deep-blue | A/20 min | faint yellow |
| 3.31 | 4-amino-3-methyl-phenol(0.06%)<br>1-naphthol(0.04%)<br>5-amino-2-methylphenol(0.03%) | rose-red | A/20 min | colorless |

Example 4:
Enzymatic Oxidized Hair Dye(a):

| | |
|---|---:|
| Stearylalcohol polyglycol ether(Steareth 20) | 1.40 g |
| Sodium sulfite | 0.10 g |
| dl-Sodium ethylenediaminetetraacetate | 0.30 g |
| D-Glucose | 1.00 g |
| Glycerol | 1.00 g |
| Isopropanol | 5.00 g |
| 1,2-Propandiol | 2.00 g |
| 1,4-Diamino-2-methylbenzene sulfate | 0.025 M |
| 5-Amino-2-methylphenol | 0.025 M |
| Glucose Oxidase (EC 1.1.3.4) | 400 units |
| Peroxidase (EC 1.11.1.7) | 400 units |
| 0.10 M Borate buffer(pH 8.5) | to 100.00 g |
| Decolorizing Gel(corresponds to B9.1): | |
| Sodium ascorbate | 5.60 g |
| Methylhydroxyethylcellulose (Tylose MHB 10,000P of Hoechst, Germany) | 1.50 g |
| Cysteine hydrochloride | 2.50 g |
| Citric acid | 5.00 g |
| Water | to 100.00 g |
| After-treatment Composition(Corresponds to B9.2): | |
| Cetrimonium chloride(50%) | 1.00 g |
| Glyoxylic acid (50%) | 1.00 g |
| Hydroxyethylcellulose | 1.50 g |
| Trisodium citrate dihydrate | 0.30 g |
| Water | ad 100.00 g |

The above-described hair dye composition (a) was applied to bleached hair. After an acting time of 60 minutes at room temperature (25° C.) the hair was washed and dried.

The deep violet colored hair was subsequently treated with the decolorizing composition B9.1 for 20 minutes at 40° C. and for 2 to 3 minutes with the after-treatment composition B9.2.

The hair was subsequently washed and dried. The hair was nearly the same color as prior to the above treatments.

Example 5: Two-component Decolorizing Emulsion

| Component 1: | |
|---|---:|
| Cetylstearyl alcohol | 4.50 g |
| Cetyl lactate | 0.50 g |
| Dimethicone | 0.50 g |
| Cetyltrimethylammonium Chloride | 0.65 g |
| Glyoxylic acid | 0.50 g |
| Water, desalenated | to 92.00 g |
| Component 2: | |
| L-Cysteine | 2.00 g |
| Ascorbic acid(powder): | 6.00 g |
| | to 100.00 g |

The component 1 is mixed with the component 2 immediately prior to use and the pH of the ready-to-use decolorizing preparation so obtained is adjusted to 2.5 with trisodium citrate dihydrate.

Example 6: Decolorizing Gel

| | |
|---|---:|
| Ascorbic acid | 8.00 g |
| L-Cysteine | 2.00 g |
| α-Ketoglutaric acid | 0.08 g |
| Hydroxyethyl cellulose | 2.00 g |
| Silica | 0.50 g |

The pH is adjusted with trisodium citrate dihydrate to 2.5 to 3.0. The mixture is mixed prior to use with 89.34 g warm water and then thoroughly stirred or mixed. The decolorizing gel so obtained can be used for decolorizing of fibers and hair which are dyed with an oxidative dye composition.

The L, a, b measured color values given in the above Tables and examples were measured with a color measuring apparatus or calorimeter, specially a Minolta Type II Chromameter.

The L-value stands for the brightness (that means the less the L-value, the more the color intensity), while the a-value is a measured of the red tones or shades (that means the greater the a-value, the greater is the proportion of reddish shades or tones in the color). The b-value is a measure of the blue proportion in the color. The more negative the b-value, the greater the amount of blue tones or shades that are present in the measured color.

The value D is a measure of the color difference between the untreated, the dyed and the bleached strands. It is determined by the following formula:

$$D=\{(L_i-L_0)^2+(a_i-a_0)^2+(b_i-b_0)\}^{1/2},$$

wherein $L_0$, $a_0$, $b_0$ are the measured color values for the untreated hair and $L_i$, $a_i$, $b_i$ are the measured color values for the treated hair. The decolorizing rate or percentage in percent is then given by the following:

Bleached %=100*[1−{D after decolorizing}/{D after dyeing}]

All percentages herein are percentages by weight, unless otherwise indicated.

The disclosure in German Patent Application 198 10 688.2-43 of Mar. 12, 1998 is incorporated here by reference. This German Patent Application describes the invention described hereinabove and claimed in the claim appended hereininbelow and provides the basis for a claim of priority for the instant invention under 35 U.S.C. 119.

While the invention has been illustrated and described as embodied in compositions and methods for dyeing and safe decolorizing of fibers, especially hair, and multi-part kit for repeatedly changing dyed fiber color, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A multi-part kit for dyeing and reductive decolorizing of fibers, said multi-part kit consisting of a first part and a second part, said first part consisting of a composition for oxidative or non-oxidative dyeing of the fibers and said second part consisting of a composition for reductive decolorizing of dyed color from the fibers, wherein said composition for reductive decolorizing of the dyed color consists essentially of a combination of at least one member selected from the group consisting of α-oxo-carboxylic acids and physiologically compatible salts of said α-oxocarboxylic acids with at least one reductone; or with at least one reductone and at least one thiol compound; or with at least one reductone and at least one sulfite compound, or with at least one reductone and at least one thiol compound and at least one sulfite compound.

2. The multi-part kit as defined in claim 1, wherein said composition for oxidative or non-oxidative dyeing contains a dye carrier comprising oxidation dye precursor compounds that form a dyeing agent on addition of an oxidizing agent to the dye carrier.

3. The multi-part kit as defined in claim 2, wherein said first part contains at least one direct-dyeing dye compound.

4. The multi-part kit as defined in claim 1, wherein said first part is a non-oxidative dyeing agent comprising direct-dyeing dye compounds.

5. The multi-part kit as defined in claim 1, wherein said composition for reductive decolorizing of dyed fibers consists essentially of from 1 to 50 percent of said at least one reductone, from 0.1 to 10 percent by weight of said at least one thiol compound, from 0.001 to 5 percent by weight of said at least one sulfite compound and from 0.1 to 10 percent by weight of said at least one member selected from the group consisting of said α-oxocarboxylic acids and said physiologically compatible salts thereof; wherein said at least one reductone is ascorbic acid, isoascorbic acid, a salt of said ascorbic acid, a salt of said isoascorbic acid, an ester of said ascorbic acid or an ester of said isoascorbic acid; and wherein said at least one member consists of glyoxylic acid, α-ketoglutaric acid, oxalacetic acid or pyruvic acid or an alkali metal salt or alkaline earth metal salt of said glyoxylic acid, said α-ketoglutaric acid, said oxalacetic acid or said pyruvic acid.

6. A method for reductive decolorizing of fibers dyed with an oxidation dye substance and/or direct-dyeing dye compounds, said method consisting essentially of the steps of:
   a) providing a composition for reductive decolorizing consisting essentially of a combination of at least one member selected from the group consisting of α-oxo-carboxylic acids and physiologically compatible salts of said α-oxocarboxylic acids with at least one reductone, or with at least one reductone and at least one thiol compound, or with at least one reductone and at least one sulfite compound, or with at least one reductone and at least one thiol compound and at least one sulfite compound;
   b) applying said composition for reductive decolorizing to said fibers; and
   c) allowing said composition to act on said fibers for a time interval of 5 to 60 minutes at a temperature of 20 to 50° C.

7. The method as defined in claim 6, wherein said composition for reductive decolorizing of dyed fibers consists essentially of from 1 to 50 percent of said at least one reductone, from 0.1 to 10 percent by weight of said at least one thiol compound, from 0.001 to 5 percent by weight of said at least one sulfite compound and from 0.1 to 10 percent by weight of said at least one member,
   wherein said at least one reductone is ascorbic acid, isoascorbic acid, a salt of said ascorbic acid, a salt of said isoascobic acid, an ester of said ascorbic acid or an ester of said isoascorbic acid; and
   wherein said at least one member consists of glyoxylic acid, α-ketoglutaric acid, oxalacetic acid or pyruvic acid or an alkali metal salt or alkaline earth metal salt of said glyoxylic acid, said α-ketoglutaric acid, said oxalacetic acid or said pyruvic acid.

8. A method for reductive decolorizing of fibers dyed with an oxidation dye substance and/or direct dyeing dye compounds, said method consisting essentially of the steps of:
   a) providing a composition for reductive decolorizing consisting essentially of at least one reductone, or at least one reductone and at least one thiol compound, or at least one reductone and at least one sulfite compound, or at least one reductone and at least one thiol compound and at least one sulfite compound;
   b) applying said composition for reductive decolorizing to said fibers;
   c) allowing said composition to act on said fibers for a time interval of 5 to 60 minutes at a temperature of 20 to 50° C.;
   d) providing a rinse composition consisting essentially of at least one α-oxocarboxylic acid or a physiologically compatible salt thereof; and
   e) treating the fibers with said rinse composition.

9. The method as defined in claim 8, wherein said rinse composition consists essentially of 0.1 to 10 percent by weight of said at least one α-oxocarboxylic acid or said physiologically compatible salt thereof.

10. The method as defined in claim 9, wherein said at least one α-oxocarboxylic acid consists of glyoxylic acid, α-ketoglutaric acid, oxalacetic acid or pyruvic acid and said physiologically compatible salt thereof is an alkali metal or alkaline earth metal salt.

11. The method as defined in claim 8, wherein said composition for reductive decolorizing of dyed fibers consists essentially of from 1 to 50 percent of said at least one reductone, from 0.1 to 10 percent by weight of said at least one thiol compound, from 0.001 to 5 percent by weight of said at least one sulfite compound, and wherein said at least one reductone is ascorbic acid, isoascorbic acid, a salt of said ascorbic acid, a salt of said isoascobic acid, an ester of said ascorbic acid or an ester of said isoascorbic acid.

12. A method for reductive decolorizing of fibers dyed with an oxidation dye substance and/or direct-dyeing dye compounds, said method consisting essentially of the steps of:
   a) providing a composition for reductive decolorizing consisting essentially of a combination of at least one reductone, or at least one reductone and at least one thiol compound, or at least one reductone and at least one sulfite compound, or at least one reductone and at least one thiol compound and at least one sulfite compound, with at least one member selected from the group consisting of α-oxocarboxylic acids and physiologically compatible salts of said α-oxocarboxylic acids;
   b) applying said composition for reductive decolorizing to said fibers;
   c) allowing said composition to act on said fibers for a time interval of 5 to 60 minutes at a temperature of 20 to 50° C.; and
   d) providing a rinse composition consisting essentially of at least one α-oxocarboxylic acid or a physiologically compatible salt thereof; and
   e) treating the fibers with said rinse composition.

13. The method as defined in claim 12, wherein said rinse composition consists essentially of 0.1 to 10 percent by weight of said at least one α-oxocarboxylic acid or said physiologically compatible salt thereof.

14. The method as defined in claim 13, wherein said at least one α-oxocarboxylic acid consists of glyoxylic acid, α-ketoglutaric acid, oxalacetic acid or pyruvic acid and said physiologically compatible salt thereof is an alkali metal or alkaline earth metal salt.

15. The method as defined in claim 12, wherein said composition for reductive decolorizing of dyed fibers consists essentially of from 1 to 50 percent of said at least one reductone, from 0.1 to 10 percent by weight of said at least one thiol compound, from 0.001 to 5 percent by weight of said at least one sulfite compound, and from 0.1 to 10 percent by weight of said at least one α-oxocarboxylic acid or said physiologically compatible salt thereof, and wherein said at least one reductone is ascorbic acid, isoascorbic acid, a salt of said ascorbic acid, a salt of said isoascobic acid, an ester of said ascorbic acid or an ester of said isoascorbic acid.

16. A multi-part kit for dyeing and reductive decolorizing of fibers, said multi-part kit consisting of a first part, a second part and a third part,
   wherein said first part consists of a composition for oxidative or non-oxidative dyeing of the fibers; said second part consists of a composition for reductive decolorizing of dyed color from the fibers, said composition for reductive decolorizing of the dyed color consisting essentially of at least one reductone, or at least one reductone and at least one thiol compound, or at least one reductone and at least one sulfite compound, or at least one reductone and at least one thiol compound and at least one sulfite compound; and said third part consists of a rinse composition consisting essentially of at least one member selected from the group consisting of α-oxocarboxylic acids and physiologically compatible salts of said α-oxocarboxylic acids.

17. A multi-part kit for dyeing and reductive decolorizing of fibers, said multi-part kit consisting of a first part, a second part and a third part;
   wherein said first part consists of a composition for oxidative or non-oxidative dyeing of the fibers; said second part consists of a composition for reductive decolorizing of dyed color from the fibers, said composition for reductive decolorizing of the dyed color consisting essentially of a combination of at least one reductone, or at least one reductone and at least one thiol compound, or at least one reductone and at least one sulfite compound, or at least one reductone and at least one thiol compound and at least one sulfite compound, with at least one member selected from the group consisting of α-oxocarboxylic acids and physiologically compatible salts of said α-oxocarboxylic acids; and said third part consists of a rinse composition consisting essentially of at least one member selected from the group consisting of α-oxocarboxylic acids and physiologically compatible salts of said α-oxocarboxylic acids.

* * * * *